(12) United States Patent
Chae

(10) Patent No.: US 10,905,446 B2
(45) Date of Patent: Feb. 2, 2021

(54) CACULUS REMOVING DEVICE

(71) Applicant: The Catholic University of Korea Industry-Academic Cooperation Foundation, Seoul (KR)

(72) Inventor: Hiun Suk Chae, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 183 days.

(21) Appl. No.: 16/080,802

(22) PCT Filed: Apr. 5, 2016

(86) PCT No.: PCT/KR2016/003503
§ 371 (c)(1),
(2) Date: Aug. 29, 2018

(87) PCT Pub. No.: WO2017/150764
PCT Pub. Date: Sep. 8, 2017

(65) Prior Publication Data
US 2019/0090891 A1    Mar. 28, 2019

(30) Foreign Application Priority Data
Feb. 29, 2016   (KR) ........................ 10-2016-0024441

(51) Int. Cl.
*A61B 17/22* (2006.01)
*A61B 17/221* (2006.01)
*A61B 17/00* (2006.01)

(52) U.S. Cl.
CPC ...... *A61B 17/22022* (2013.01); *A61B 17/221* (2013.01); *A61B 17/2202* (2013.01);
(Continued)

(58) Field of Classification Search
CPC ........ A61B 17/22022; A61B 17/22012; A61B 17/221; A61B 2017/00862; A61B 2017/22038
(Continued)

(56) References Cited

U.S. PATENT DOCUMENTS 4,741,335 A * 5/1988 Okada ................. A61B 17/221
                                                      606/127
5,376,094 A * 12/1994 Kline .................. A61B 17/221
                                                      606/110
(Continued)

FOREIGN PATENT DOCUMENTS

KR    10-0928706 B1    11/2009

OTHER PUBLICATIONS

International Search Report dated Oct. 21, 2016 in connection with PCT/KR20016/003503.

*Primary Examiner* — Tuan V Nguyen
(74) *Attorney, Agent, or Firm* — Akerman LLP

(57) ABSTRACT

The present disclosure relates to a calculus removing device which is used in the medical field. More particular, the present disclosure relates to a calculus removing device which has a lithotripsy probe capable of simultaneously destructing and removing the calculus formed in the human body regardless of the size of the calculus by optionally using attractivity or electricity through a lithotripsy probe. According to an embodiment of the present disclosure, a calculus removing device includes a first tube having an interior region; a second tube which is inserted in to the interior region of the first tube so as to move in the interior region; a capture means of which one end is coupled to an end of the second tube, and which is led-in into the interior region of the first tube corresponding to the moving of the second tube, allowing capturing and fixing a calculus; a lithotripsy probe which is inserted into an interior region of (Continued)

the second tube and contacts with the calculus fixed by the capture means, allowing applying an electric shock; and a handle which is coupled to an end of the first tube, and moves the second tube and the lithotripsy probe independently.

10 Claims, 11 Drawing Sheets

(52) U.S. Cl.
CPC .. *A61B 17/22012* (2013.01); *A61B 17/00234* (2013.01); *A61B 2017/00818* (2013.01); *A61B 2017/00862* (2013.01); *A61B 2017/22008* (2013.01); *A61B 2017/2215* (2013.01); *A61B 2017/22021* (2013.01); *A61B 2017/22025* (2013.01); *A61B 2017/22038* (2013.01)

(58) Field of Classification Search
USPC ................................ 606/113, 127, 110, 128
See application file for complete search history.

(56) References Cited

U.S. PATENT DOCUMENTS

| | | |
|---|---|---|
| 6,500,182 B2 | 12/2002 | Foster |
| 8,092,470 B2 | 1/2012 | Miyamoto et al. |
| 8,562,601 B2* | 10/2013 | Yanuma ................ A61B 17/22 606/39 |
| 2005/0033314 A1 | 2/2005 | Sakurai et al. |
| 2008/0188866 A1 | 8/2008 | Karpiel et al. |
| 2013/0046297 A1* | 2/2013 | Lingeman ............ A61B 17/221 606/41 |
| 2013/0079797 A1 | 3/2013 | Diamant, I et al. |

* cited by examiner

【FIG. 1】
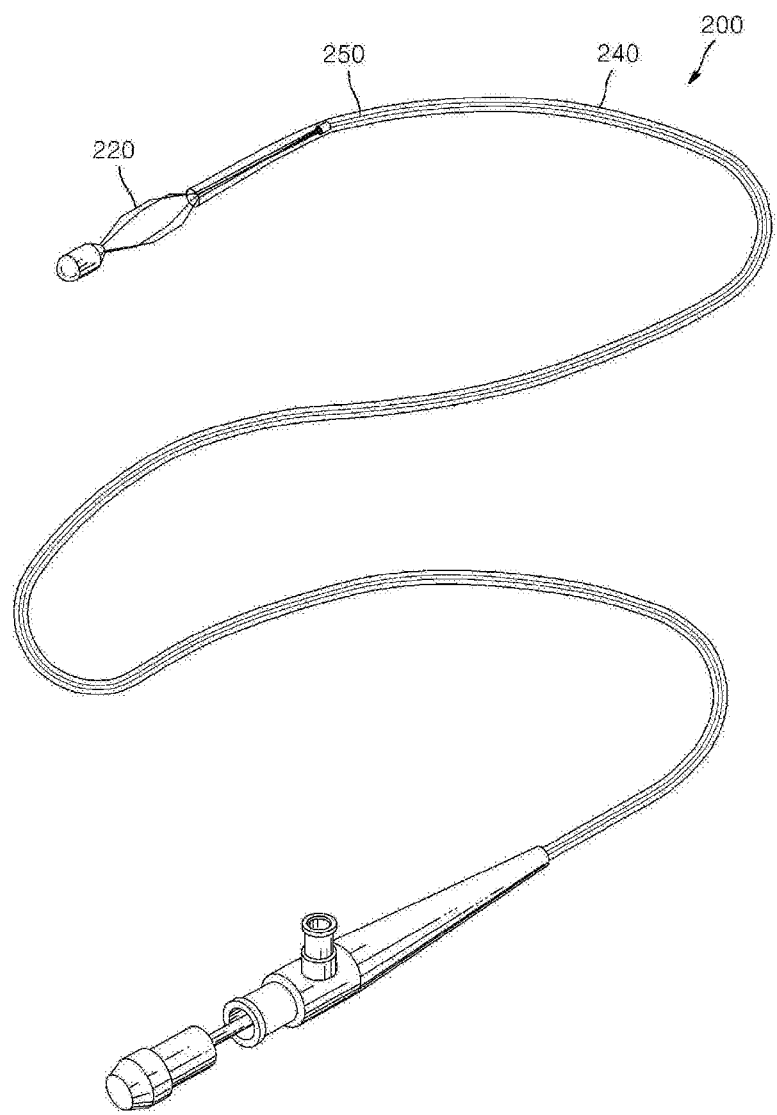

[FIG. 2]
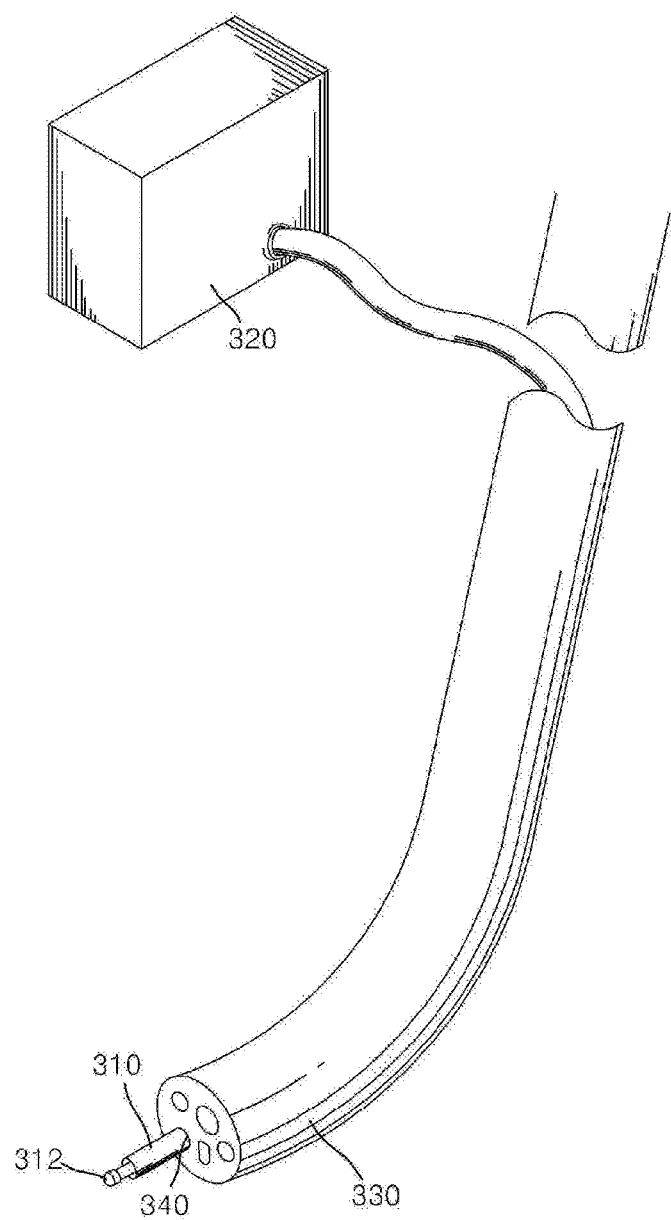

[FIG. 3]
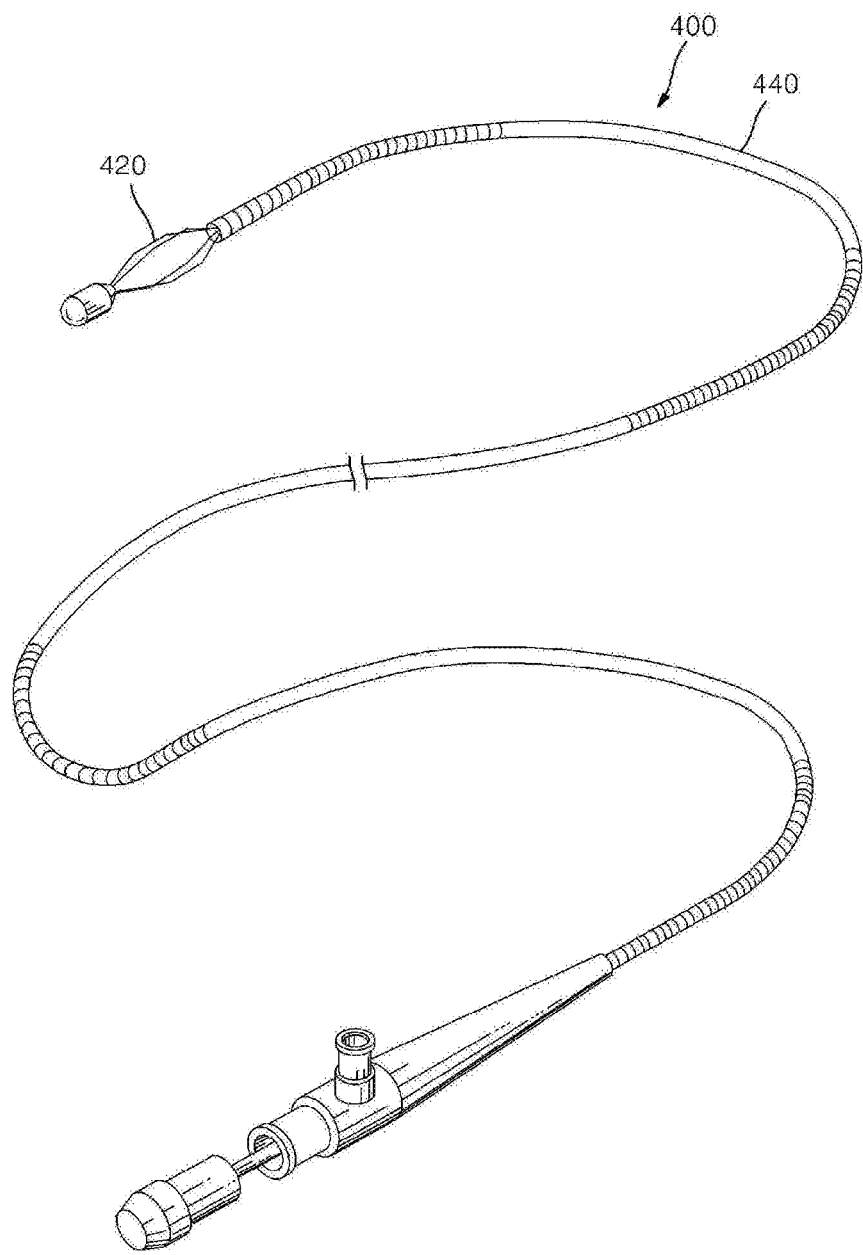

[FIG. 4]
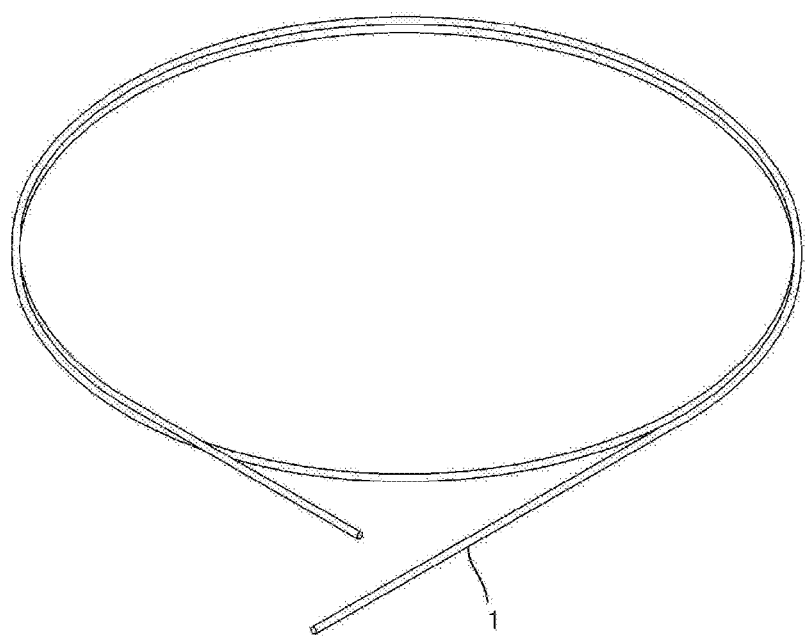

[FIG. 5]
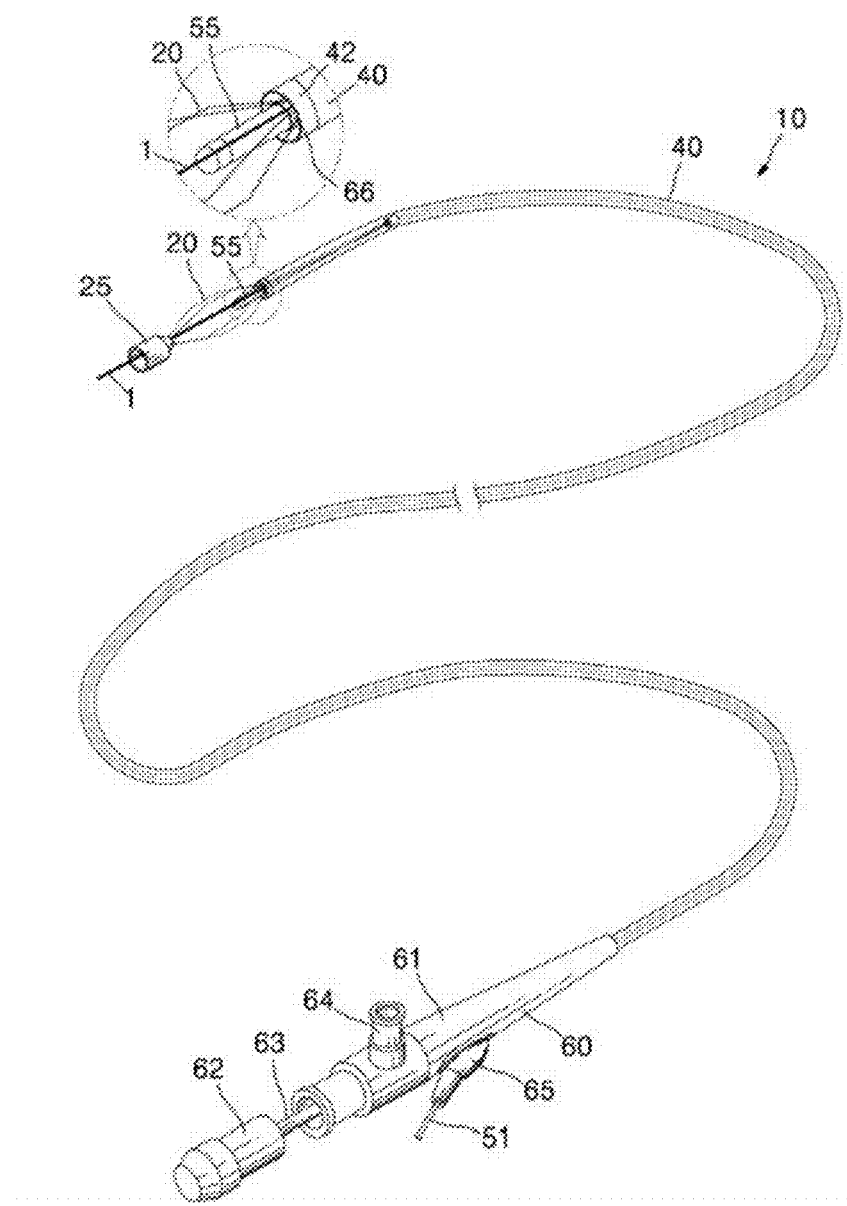

[FIG. 6]
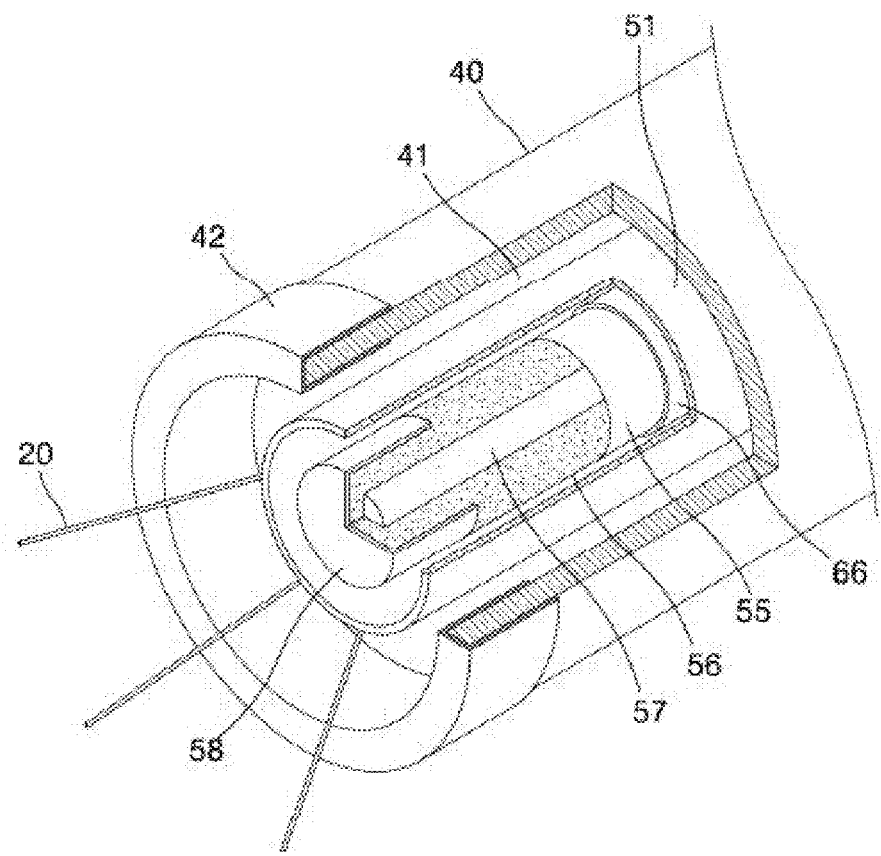

[FIG. 7]
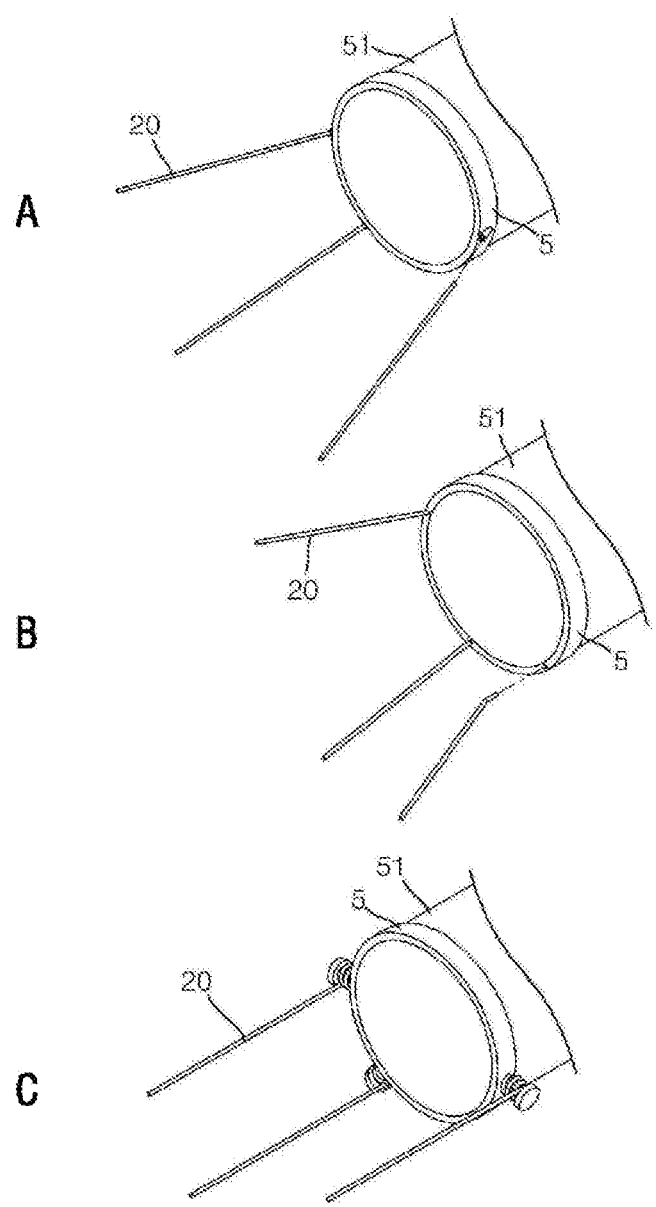

[FIG. 8]
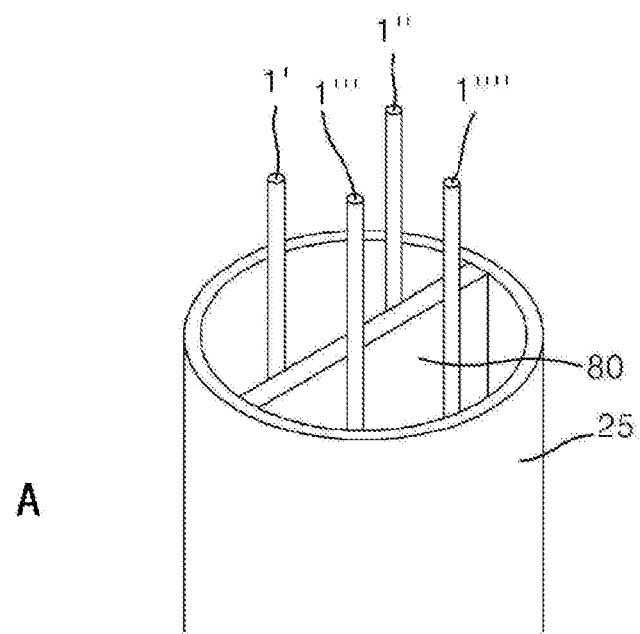
A
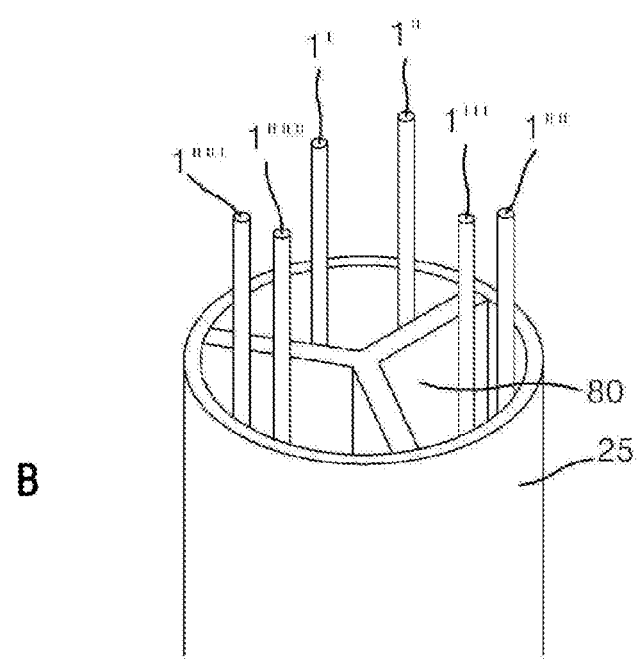
B

[FIG. 9]
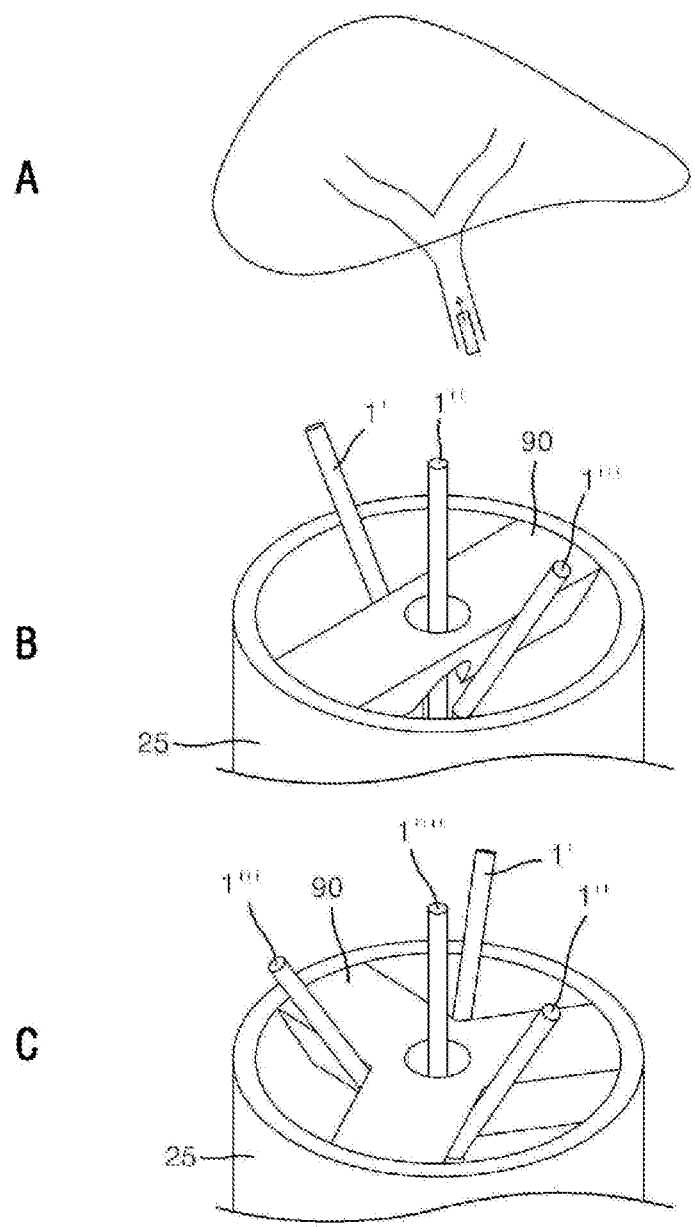

[FIG. 10]
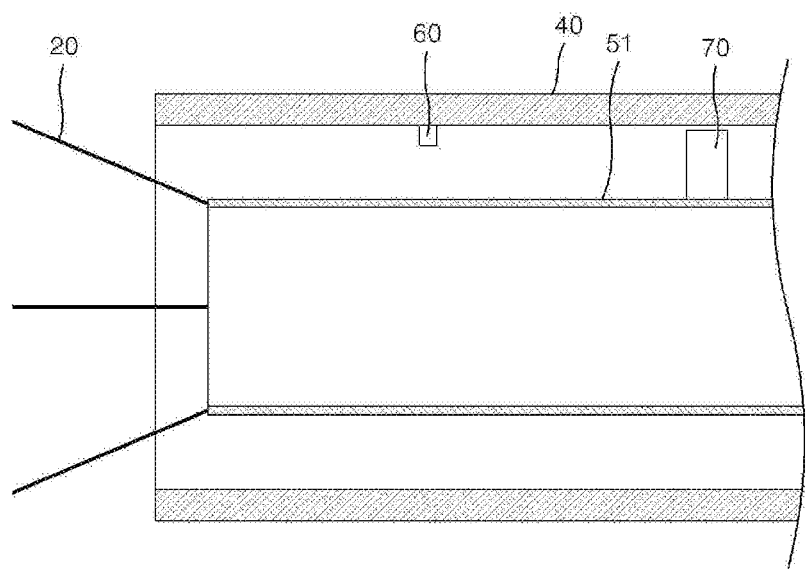

[FIG. 11]
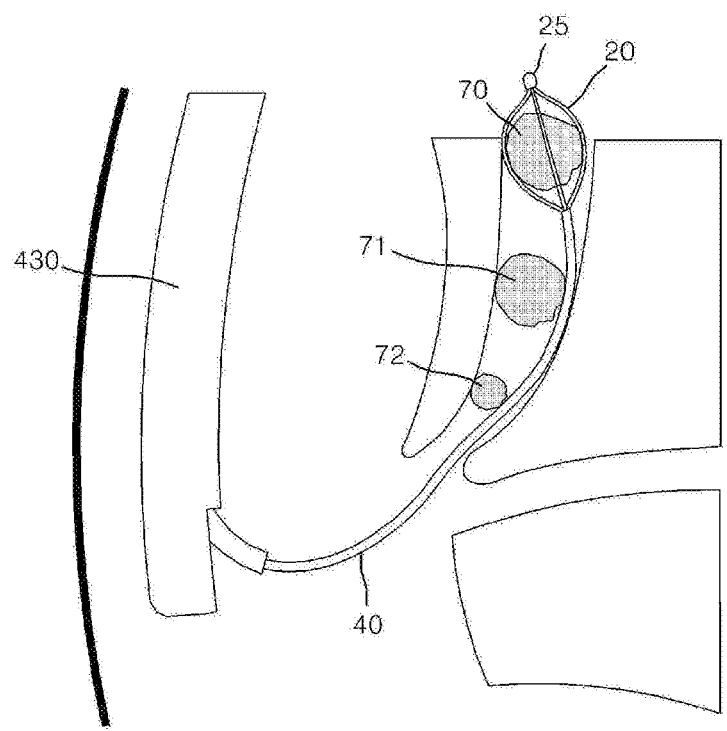

CACULUS REMOVING DEVICE

This application is a national phase of PCT/KR2016/003503, filed Apr. 5, 2016, and claims priority to KR 10-2016-0024441, filed Feb. 29, 2016, the entire contents of both of which are hereby incorporated by reference.

BACKGROUND

Technical Field

The present disclosure relates to a calculus removing device, more specifically to a calculus removing device which has a lithotripsy probe capable of simultaneously destructing and removing the calculus formed in the human body regardless of the size of the calculus by optionally using attractivity or electricity through a lithotripsy probe.

Description of the Related Art

Commonly, the formation of calculi in the human body is influenced by ion deposits by the change in solubility according to the change in pH. The calculi may be classified into a ureteric calculus, a bile duct calculus (gallstone) and the like according to the area where calculi occur. When these calculi occur, these allow flow disorder and cause any symptoms according thereto. There are diverse methods for removing such calculi, and commonly are used endoscopy, basket catheters, and electrohydraulic lithotripters having a lithotripsy probe.

As such an example, the removal of calculi after performing sphincterotomy and devices used therefor will be discussed herein.

A bile duct calculus having a diameter of no more than 10 mm may be removed approximately 90% using conventionally used sphincterotomy and a basket or a balloon. However, it is impossible to remove a gallstone having a diameter of 10 mm or more by the above described methods and thus the gallstone may be removed after destruction of a calculus. Techniques for destruction of a calculus may be widely classified into mechanical lithotripsy and electrohydraulic lithotripter. In particular, a bile duct calculus having a diameter of within 10 mm may be recovered using a basket catheter after endoscopic sphincterotomy. However, a calculus having a diameter of 10 to 20 mm may be removed using a basket catheter by destruction immediately after endoscopic sphincterotomy.

FIG. 1 is a perspective view of a basket catheter commonly used for lithotripsy.

Referring to FIG. 1, a basket catheter 200 may be structured so that four strands of wires 250 formed by twisting metal wires are inserted into an interior region of a tube 240, four strands of the wires 250 are fixed to the tip ends of the wires, the respective wires 250 are bent and ends thereof are fixed, allowing the formation of a basket 220. As reviewing operation for removing the gallstone, the tip end of the tube 240 is inserted to the position where a bile duct calculus occurs. The basket 220 is then opened so as to capture the bile duct calculus in the basket 220. Subsequently, the basket 220 is pulled into the tube 240 and the gallstone is taken out in a state of tightened up and fixed to the basket, allowing the removal of the bile duct calculus.

However, the removal of a bile duct calculus using such a basket catheter may be limited to the size and position of the bile duct calculus. When the bile duct calculus has a long diameter of 10 mm or more, it may be difficult to remove such a calculus. Also, it may be still difficult to remove a giant calculus having a long diameter of 20 mm or more even if performing sphincterotomy.

In addition, it is required to guide by a guide wire in advance, so as to provide a calculus through the basket catheter 200. If applying one guide wire, there may be problems that the position of the basket catheter 200 itself is frequently changed, and a user could not send the guide wire to a desired place.

Therefore, it is required a device and a method allowing the user to send a plurality of the guide wires to a desired place and efficiently removing a calculus regardless of the size of the calculus.

SUMMARY OF THE INVENTION

The present invention relates to a calculus removing device which has a lithotripsy probe capable of simultaneously destructing and removing the calculus formed in the human body regardless of the size of the calculus by optionally using attractivity or electricity through a lithotripsy probe.

Further, the present invention relates to a calculus removing device which requires a few people for the operation, is easily operated even by a less skilled person, shortens operation time and is excellent in destruction of a calculus, allowing easy and safe operation while reducing pain of a patient, and reduces manufacturing costs.

Further, the present invention relates to a calculus removing device which allows the insertion of a guide wire for guiding a basket catheter into the interior region of a second tube, wherein a plurality of the guide wires may be applied using structural features of the end of a first tube, so as to enhance fixability or send the guide wires to the directions that user desires.

Meanwhile, the present invention is not limited to the above-mentioned technical problems, and unless specifically stated otherwise herein, other technical problems will be clearly understood by those of ordinary skilled in the art from the following description.

A first aspect of the present invention is characterized by a calculus removing device may include: a calculus a first tube having an interior region; a second tube which is inserted into the interior region of the first tube so as to move in the interior region; a capture means of which one end is coupled to an end of the second tube, and which is led-in into the interior region of the first tube corresponding to the moving of the second tube, allowing capturing and fixing a calculus; a lithotripsy probe which is inserted into an interior region of the second tube and contacts with the calculus fixed by the capture means, allowing applying an electric shock; and a handle which is coupled to an end of the first tube, and moves the second tube and the lithotripsy probe independently, wherein the capture means further comprises, at an opposite end, a head portion which is at least partially opened and has a diameter larger than that of the first tube, a plurality of guide wires for guiding the calculus removing device is inserted through the interior region of the second tube, the plurality of guide wires inserted is discharged to the outside through the head portion, and the capture means is a basket configured with at least two or more wires having elasticity.

Another aspect of the present invention is any such device wherein: if a size of the calculus is less than a predetermined size, the calculus fixed by the capture means may be removed as the handle is pulled, and if a size of the calculus exceeds the predetermined size, the calculus fixed by the capture means may be removed by the applied an electrical shock.

Another aspect of the present invention is any such device wherein: the capture means may be coupled with an end of the second tube using at least one of methods as follows; a method which allows the insertion of the capture means formed at the end of the second tube, a method which allows the insertion of the capture means into a hole formed at the end of the second tube, and a method which allows the capture means in a state of being winded up around a member formed at the end of the second tube to be unwound corresponding to the rotation of the member and comes out to the outside.

Another aspect of the present invention is any such device wherein: the head portion further may include, in an opened space, a separating member which is separated into a plurality of regions, wherein the plurality of guide wires inserted may be separated to the at least a portion of the plurality of regions, allowing discharge to the outside, and the separating member may be detachable.

Another aspect of the present invention is any such device wherein: the separating member may become thicker toward an end of the head portion, and the plurality of guide wires may be bent at a predetermined angle using a thickness of the separating member, allowing discharge to the outside.

The present invention may provide a user with a calculus removing device which has a lithotripsy probe capable of simultaneously destructing and removing the calculus formed in the human body regardless of the size of the calculus by optionally using attractivity or electricity through a lithotripsy probe.

Further, a calculus removing device according to the present invention may allow the insertion of a guide wire for guiding a basket catheter into the interior region of a second tube, wherein a plurality of the guide wires may be applied using structural features of the end of a first tube, so as to enhance fixability or send the guide wires to the directions that user desires.

Further, a calculus removing device according to the present invention may allow capturing and destructing various calculi using one device. Thus, the device may not require to use any of cholangioscopy, basket catheters and electrohydraulic lithotripters separately.

Further, a calculus removing device according to the present invention, may allow performing an operation directly while watching an X-ray image. Thus, the device may not require any of a high-priced endoscope for operating an electrohydraulic lithotripter separately and inserted into the endoscope, allowing identifying a calculus using the endoscope and subsequently destructing and removing the calculus.

Further, a calculus removing device according to the present invention may allow easy and simple lithotripsy by a lithotripsy probe differently from using the conventional mechanical lithotripsy basket catheter without frequent insertion.

Further, a calculus removing device according to the present invention may allow capturing and destructing various calculi using one device. Thus the device may not require people necessary to operate conventionally devices needed for removing the respective calculi, allowing one person to perform an operation.

Further, since, in a state that a calculus is fixed by a capture means, the lithotripsy probe is placed at the center portion of the calculus and applies a shock to the calculus at the nearest distance, a shock wave may be transferred to the center portion of the calculus. Thus, it may excellent in the shock effect and involve no damage to the normal bile duct resulting from wobbling of the lithotripsy probe.

Further, the first tube is inserted into the bile duct, allowing the destruction of a calculus in the bile duct. Even if it is difficult to perform sphincterotomy, the calculus may be destructed at various times, allowing removing the calculus easily and simply by inserting the endoscope only once.

Further, calculi may be removed regardless of the order of the respective calculi which are developed on a near region and a far region.

Additionally, when a calculus and a cancer uncommonly present together, it may be possible to perform cytology test for a diagnosis of the cancer.

Meanwhile, effects of the present invention are not limited to the aforementioned effects, and other effects not covered will be clearly understood to those of ordinary skilled in the art from the following description.

BRIEF DESCRIPTION OF THE DRAWINGS

FIG. 1 is a perspective view of a usual basket catheter used in removing a bile duct calculus.

FIG. 2 is a perspective view which shows a state that a lithotripsy probe of an electrohydraulic lithotripter is inserted into the endoscope.

FIG. 3 is a perspective view of a mechanical lithotripsy basket catheter.

FIG. 4 shows a particular embodiment of a guide wire capable of used together in the present invention.

FIG. 5 is a perspective view of one embodiment of a calculus removing device according to the present invention.

FIG. 6 is a sectional view of the structure of partially cut such an embodiment in FIG. 5.

FIG. 7 shows a particular embodiment in which a basket wire is coupled with an end of a second tube in a calculus removing device according to the present invention.

FIG. 8 shows a particular embodiment of an end of a first tube to which a plurality of guide wires is applied in a calculus removing device according to the present invention.

FIG. 9 shows a particular embodiment of a guide which allows a user to send a plurality of guide wires to a desired direction in a body in a calculus removing device according to the present invention.

FIG. 10 shows a particular embodiment which includes a stopper allowing preventing a basket wire of an end of a second tube from being discharged at more than a predetermined length to the outside, according to the present invention.

FIG. 11 is a phase view in which a calculus is removed by a calculus removing device according to the present invention.

DETAILED DESCRIPTION OF THE EMBODIMENTS

As described in the technical field above referring to FIG. 1, the removal of a bile duct calculus using a basket catheter has limits according to the size of the calculus and the area where such a calculus occurs. In practice, when a long diameter of a bile duct calculus is 10 mm or more, it is difficult to remove the calculus. In addition, it is difficult to remove a giant calculus having a long diameter of 20 mm or more even though performing sphincterotomy.

Further, it is required to the guide of a guide wire in advance so as to provide a calculus through a basket catheter

200, wherein if applying only one guide wire, the position of the basket catheter 200 itself is changed frequently and it is difficult for a user to send the guide wire to a desired place.

A mechanical lithotripsy basket catheter and an electrohydraulic lithotripter are designated so as to overcome the aforementioned limits and a giant calculus having a long diameter of 30 mm or more may be removed thereby.

FIG. 2 is a perspective view which shows a state that a lithotripsy probe of an electrohydraulic lithotripter is inserted into the endoscope.

Referring to FIG. 2, an electrohydraulic lithotripter includes an electrohydraulic lithotripsy shock wave generator 320 and a lithotripsy probe 310. The lithotripsy probe 310 may be discharged to a high voltage of 188-2000V at its tip end of a discharge electrode 312 in a moment by a voltage supplied from the electrohydraulic lithotripsy shock wave generator 320, allowing generating a shock wave having a discharge energy of 0.6-5 ws. A bile duct calculus may be positioned in the front of an endoscope 330 and then the lithotripsy probe 310 may be protruded through a forceps 340 of an endoscope 330 allowing the discharge electrode 312 at the tip end to approach or contacted to the calculus, followed by discharge and destruction. The destructed calculus may be removed by natural evacuation or using a basket catheter.

FIG. 3 is a perspective view of a mechanical lithotripsy basket catheter.

Referring to FIG. 3, this mechanical lithotripsy basket catheter 400 may be similar to the structure of the aforementioned basket catheter, however, such a basket catheter may be characterized in that a tube 440 into which a basket 420 is inserted is made of a metal. A tip end of the tube 440 of the basket catheter 400 may be inserted toward a position of a calculus and then the basket 420 may be opened allowing capturing the calculus into the basket 420. The basket 420 may be inserted into the metal based tube 440 forcibly by a person, allowing destructing the bile duct calculus by a physical force. The destructed calculus may be captured with the basket 420, allowing removed by natural evacuation or using a basket catheter.

However, when removing a calculus using the mechanical lithotripsy basket catheter, some problems may occur. Firstly, since when removing a calculus using the mechanical lithotripsy basket catheter, the basket capturing the calculus should be inserted into the metal based tube by adding force, it may take a long time for destruction. In addition, since the metal based tube has a low flexibility and is thus difficult operated, an operator may need to be well skilled. Further, since a size of the basket has a limit, it may be difficult to destruct a calculus having a size of 30 mm or more. If it is impossible to perform sufficient sphincterotomy (e.g. duodenal diverticulum), it may be required to perform lithotripsy several times, the time for destruction may become longer, a patient may have pain, and conventionally a calculus occurring on a near region should be destructed earlier than a calculus occurring on a far region.

Further, if removing a calculus using an electrohydraulic lithotripter, since it is required to observe a calculus directly, allowing removing it, a special-purpose, high-priced cholangioscopy (percutaneous transhepatic cholangioscopy, transpapillary cholangioscopy) should be involved at the same time, and an operator may feel uncomfortable aiming a center position of a calculus exactly after identifying the calculus with an endoscope. In addition, it is required to insert a basket catheter separately after destruction using a lithotripsy probe, so as to remove a calculus entirely. Accordingly, at least two of well skilled operators may be needed to control an endoscope beside an electrohydraulic lithotripter, so as to perform the operation and it may be even difficult to perform the operation. When using endoscopy including percutaneous transhepatic cholangioscopy and transpapillary cholangioscopy, total 2 or 3 or more assist persons may be needed.

In addition, it is required to guide by a guide wire in advance, so as to provide a calculus through the basket catheter. If applying one guide wire, there may be problems that the position of the basket catheter itself is frequently changed, and a user could not send the guide wire to a desired place. There is neither devices nor methods to solve these problems heretofore. Therefore, the present invention relates to a calculus removing device which has a lithotripsy probe capable of simultaneously destructing and removing the calculus formed in the human body regardless of the size of the calculus by optionally using attractivity or electricity through a lithotripsy probe.

Further, the present invention relates to a calculus removing device which requires a few people for the operation, is easily operated even by a less skilled person, shortens operation time and is excellent in destruction of a calculus, allowing easy and safe operation while reducing pain of a patient, and reduces manufacturing costs.

Further, the present invention relates to a calculus removing device which allows the insertion of a guide wire for guiding a basket catheter into the interior region of a second tube, wherein a plurality of the guide wires may be applied using structural features of the end of a first tube, so as to enhance fixability or send the guide wires to the directions that user desires.

As referring to FIG. 4, a guide wire is described prior to the explanation of a structure according to the present invention.

FIG. 4 shows a particular embodiment of a guide wire capable of used together in the present invention.

So as to lead either an angiographic catheter or a cardiac catheter to an aimed blood vessel, a guide wire 1 illustrated in FIG. 4 may be an extremely thin steel wire which is used for insertion into an interior of the catheter.

The guide wire 1 may be structured by covering a lead helically around a steel wire with an extremely thin steel wire and welding a semi-spherical shaped steel wire having excellent elasticity and flexibility at an end.

The entire guide wire 1 may be processed with Teflon, allowing to reduce a damage to a blood vessel resulting from either breakage or bending in the blood vessel when undergoing a test.

The end of the guide wire 1 may have a semi-spherical shape and sorted into a J type and a straight type. A "J" typed wire may be often used for tortuous vessel, arteriosclerosis and elderly patients, allowing preventing the vessel wall from being damaged.

Commonly, the guide wire 1 may be inserted to a surgical region and then a calculus removing device may be inserted into the body along the inserted guide wire.

At this time, if applying one guide wire, it may be difficult to support a calculus removing device when inserted into the body, and even if reaching to a desired position, it may be also difficult to maintain such device in a state of fixed without any movements in a relevant position.

Therefore, it is preferable to use a plurality of guide wires rather than only one guide wire, allowing the calculus removing device inserted through the plurality of guide wire to be easily inserted into the body and maintained in a state of fixed in the desired position.

However, prior art provides neither methods nor devices for inserting a plurality of guide wires. Therefore, the present invention may provide a solution for a problem as such.

FIG. 5 is a perspective view of one embodiment of a calculus removing device according to the present invention.

So as to achieve the aforementioned object, a calculus removing device may include a first tube having an interior region, a second tube which is inserted into the interior region of the first tube, a capture means of which one end is coupled to an end of the second tube, and which is led-in into the interior region of the first tube, allowing capturing and fixing a calculus, a lithotripsy probe which is inserted into an interior region of the second tube and contacts with the calculus fixed by the capture means, allowing applying an electric shock, and a handle which is coupled to an end of the first tube and moves the second tube and the lithotripsy probe independently The capture means may be preferably formed into a basket shape using a plurality of metal thin wires having an elasticity, allowing giving an advantage in fixing a calculus to the first tube.

Further, the first tube and the second tube may be preferably made of a plastic material and tip ends thereof may be covered with a metal material, allowing preventing the first tube and the second tube from damaged by force added when adhering a calculus, and also allowing showing such first and second tubes on an X-ray image very well.

Referring to drawings, basket catheters are hereinafter described as embodiments of a calculus removing device which has a lithotripsy probe according to the present invention. However, the basket catheters are only embodiments of the present invention and not limitative to the present invention.

Referring to FIGS. 5 and 6, a basket catheter 10, as a calculus removing device according to the present invention, may include a basket 20 for capturing a calculus, a first tube 40 which guides the first tube 40 to a position of the calculus, a lithotripsy probe 55 which applies a shock wave to the calculus, a second tube 51 into which the lithotripsy probe 55 is inserted, and a handle which control movements of the second tube 51, the basket 20 and the lithotripsy probe 55.

The basket 20 may be structured to be coupled to an end of the second tube 51, allowing entering an end portion of one side of the first tube 40, and the entering thereof may be controlled by the handle 60 coupled to another end portion of the opposite side of the first tube 40.

The first tube 40 may be made of a plastic material, allowing having a flexibility, and a length and diameter of the first tube 40 may be changed if necessary.

Further, the first tube 40 may be covered up with a metal material, allowing forming a tube protecting portion 42 at the end portion of one side of the first tube 40.

Wherein, the first tube 40 may be made of a transparent or semi-transparent material such as a Teflon material, allowing the interior thereof to be shown.

The second tube 51 may be inserted into an interior region 41 of the first tube 40, and an tip end of one side of the second tube may be coupled to the handle 60 at another tip end of the opposite side therethrough.

The basket 20 may be made of a plurality of metal thin wires having flexibility, allowing forming a basket shape when such basket is discharged to an outer side of the first tube 40. A head portion 25 may be coupled to a tip end of the basket 20.

The basket 20 may be moved along the second tube 51.

Wherein, the head portion 25 may have a size enough to close the interior region 41 of the first tube 40 when the first tube 40 is moved to a position of a calculus. A tip end thereof may be processed smoothly edged, allowing preventing damages to the human body tissue.

In addition, an end of the head portion 25 may be formed to be opened toward the outside, allowing the guide wire 1 to be discharged to the outside through the opened end.

The number of the metal thin wires constituting the basket 20 may be increased or decreased if necessary.

An interior region of the second tube 51 may penetrate a space in-between the second tube 51 and the first tube 40, allowing the lithotripsy probe 55 to be inserted.

The lithotripsy probe 55 may embed a conductive lead 57 having electrical conductivity inside a probe body 56. The conductive lead 57 may be electrically coupled with a discharge electrode 58 which is coupled to an end of the probe body 56.

If applying electricity to the lithotripsy probe 55, a high voltage of 1800 to 2000V may be applied to the discharge electrode 58 of the tip end thereof, allowing generating a shock wave having a discharge energy.

The handle 60 coupled to the end of one side of the first tube 40 may be structured to include a steel lead 63 coupled with the second tube, a pushing portion 62 coupled with the steel lead, an injection portion 64 for injecting contrast media, saline solution and the like which are necessary for removing a calculus, and a lithotripsy probe discharging portion 64 in which a pipe coupled with the lithotripsy probe 55 is discharged to the outside, allowing the lithotripsy probe 55 included in the second tube 51 to be discharge to the outside.

That is, if a user pushes the pipe 66 of the lithotripsy discharging portion 65, connected with the lithotripsy probe 55 forwardly, the lithotripsy probe discharging portion 65 inside the second tube 51 may be discharged to the outside and a length of the discharged lithotripsy probe 55 may lengthen enough, allowing such discharged lithotripsy probe to be easily coupled with a voltage generator (not illustrated) for applying electricity to the lithotripsy probe 55.

The aforementioned guide wire 1 may be discharged to the outside through the space in-between the second tube 51. The guide wire 1 discharged from the second tube 51 may be discharged to the outside through an empty space of a last end of the head portion 25.

Referring to FIG. 7, a specific structure according to the present invention is described.

FIG. 7 shows a particular embodiment in which a basket wire is coupled with an end of a second tube in a calculus removing device according to the present invention.

Basically the basket catheter 10 according to the present invention may be embodied in two or three of tubes.

In such a case of using two of tubes, the basket tube 20 may be coupled to the first tube 40. However, if coupling the basket wire 20 to the first tube 40, the basket wire 20 flexibly may be moved and thus it may be difficult to fix a calculus. Further, in such a case of using three of tubes, a thickness of the basket catheter 10 itself may be too thick to be easily inserted into the body.

Therefore, according to the present invention, even two of tubes may be used so as to reduce the total volume of an entire device, the basket wire 20 may be coupled to not the first tube 40 but the second tube 51.

Further, a band 5 may be used in a structure to couple the basket wire 20 to the second tube 51 and the band may be manufactured into a metal type.

However, considering a leak current that may be caused by characteristics of the metal, a cover made of a plastic material may be further included on a surface of the metal.

Referring to the drawing, a specific coupling type may be described.

As shown in A of FIG. 7, the structure to couple the basket wire 20 to the second tube 51 may be embodied in that a plurality of insertion portions may be formed on the surface of the second tube 51 and the basket wire 20 may be put in the plurality of insertion portions.

Further, as shown in B of FIG. 7, the structure to couple the basket wire 20 to the second tube 51 may be embodied in that a plurality of holes may be formed on the surface of the second tube 51 and the basket wire 20 may be put in the plurality of holes.

Further, as shown in C of FIG. 7, the structure to couple the basket wire 20 to the second tube 51 may be embodied in that a plurality of skein typed structures, that is, the basket wire 20 is wound may be formed in the end of the first tube 51 and the skein typed structures may be unwound, allowing the basket wire 20 to be discharged to the outside.

As aforementioned, a structure to apply a plurality of guide wires 1 is described hereinafter.

FIG. 8 shows a particular embodiment of an end of a first tube to which a plurality of guide wires is applied in a calculus removing device according to the present invention. It may be possible to involve a detachable member for closing a hole in the center.

According to the present invention, a separating member 80 may be used for separating the end of the head portion 25 into a plurality of regions, so as to put the plurality of guide wires 1 therein.

The separating member 80 may be detachably coupled to the end of the head portion 25 in which the basket wire 20 may be discharged to the outside.

As shown in A of FIG. 8, the end of the head portion 25 in which the guide wire 1 may be discharged to the outside through the separating member 80 may be separated into two regions. The guide wire 1 may be discharged to the respective two regions, allowing the plurality of wires 1 to be discharged.

Furthermore, the plurality of the guide wires 1', 1'', 1''', 1'''' etc., may be put in the respective separated regions themselves, allowing applying more of the guide wires.

Further, as shown in B of FIG. 8, the end of the head portion 25 in which the guide wire 1 may be discharged to the outside through the separating member 80 may be separated into three regions. The guide wire 1 may be discharged to the respective three regions, allowing the plurality of wires 1 to be discharged.

Like the proceeding, the plurality of the guide wires 1', 1'', 1''', 1'''' etc., may be put in the respective separated regions themselves, allowing applying more of the guide wires.

Meanwhile, when inserting the guide wire 1 into an organ such as liver and the like, an inserted pipes may be formed into a shape toward not only one of but a plurality of directions.

FIG. 9 shows a particular embodiment that a user positions a plurality of guide wires so that the guide wires may reach a desired direction in the intrahepatic bile duct in a calculus removing device according to the present invention.

Referring to A of FIG. 9, as an example, a calculus may occur in a position not outside of but inside of the liver.

Like A of FIG. 9, if a pathway for inserting the guide wire 1 may be divided into two parts, it may be difficult to insert the guide wire 1.

Beside the exemplary situation, a special situation in which the pathway for inserting the guide wire 1 may be divided into three parts may occur.

Therefore, according to the present invention, a guide member 90 may be formed to guide the plurality of guide wires 1 to a desired direction in advance, allowing the guide wire 1 to be inserted to the desired direction at the end of the head portion 25.

The guide member 90 may be detachably coupled to the end of the head portion 25 in which the guide wire 1 may be discharged to the outside.

Further, the guide member 90 becomes thicker toward the end of the head portion, allowing discharging the guide wire 1, which is discharged to the outside, in a state of being bent in the desired direction.

According to a structure of B of FIG. 9, the plurality of guide wires 1 may be divided into two parts and then discharged. According to a structure of C of FIG. 9, the plurality of guide wires 1 may be divided into three parts and then discharged at a predetermined angle.

Further, considering a basic direction, a space for discharging the guide wire 1 inserted linearly may be further formed in the center of the guide member 90 of B and C of FIG. 9.

Meanwhile, if the second tube 51 may be discharged too much, the basket wire 20 may be also much discharged to the outside, resulting in inducement of malfunction and failure of such basket wire or causing some cases that such basket wire hardly captures a calculus.

Therefore, according to the present invention, a stopper is provided, allowing preventing the second tube 51 from being discharged too much to the outside, so as to apply a method such that the basket wire 20 may be discharged to the outside by a predetermined distance.

FIG. 10 shows a particular embodiment which includes a stopper allowing preventing a basket wire of an end of a second tube from being discharged at more than a predetermined length to the outside, according to the present invention.

Referring to FIG. 10, a first protrusion 70 may be formed in a portion of an outer wall of the second tube 51, and the first protrusion 70 may be extended to an inner wall of the first tube 40.

Further, referring to FIG. 10, a second protrusion 60 may be formed in a portion of the first tube 40. If the first protrusion 70 may be moved to the portion where the second protrusion 60 is formed, such the first protrusion cannot be moved toward the end of the first tube 40 anymore.

Therefore, the basket wire 20 coupled to the end of the second tube 51 may not be discharged to the outside exceeding a predetermined distance.

Further, the lithotripsy probe 55 inserted into the second tube 51 may be structured to be discharged from the second tube 51, and thus such lithotripsy probe may be discharged from the second tube 51 regardless of the stopper, allowing being contacted with a calculus pulled into the second tube.

Procedures for removing a calculus using the aforementioned basket catheter 10 is described hereinafter.

FIG. 11 is a phase view in which a calculus is removed by a calculus removing device according to the present invention.

However, FIG. 11 shows a phase performed by using an endoscope 430. But, the basket catheter 10 may be directly used without using the endoscope 430.

Considering sequential procedures of the operation, when a long diameter of a calculus is 10 mm or under, an operator may pull the pushing portion 62 of the handle 60, allowing pulling the second tube 51 toward the handle and consequently allowing the basket wire 20 to be pulled into the interior region 41 of the first tube 40.

At this time, the head portion 25 coupled with the basket wire 20 may close the interior region 41 of the first tube 40.

In this state, the operator may send the tip end of the first tube 40 of the basket catheter 10 to a position where a calculus 72 occurs, watching an X-ray image using the conventional endoscope 430, separately.

When the tip end of the first tube 40 reaches to the position of the calculus 72, the operator may continuously push the pushing portion 62, watching the X-ray image, allowing pulling the calculus 72 into the inner side of the basket wire 20. After then operator may pull the pushing portion 62.

The basket wire 20 may be led-in into the interior region 41 of the first tube 40 and the calculus 72 may be closely fixed to the tip end of the first tube 40 at the same time.

In this state, the captured calculus 72 may be removed by taking out the first tube 40 or the second tube 51.

Meanwhile, when a long diameter of a calculus is 10 mm or more, the operation allowing the tip end of the first tube 40 to reach a position of a calculus is the same as the case when a size of a calculus is small.

When the tip end of the first tube 40 may reach the position of the calculus 70, the operator may continuously push the pushing portion 62, watching the X-ray image, allowing pulling the calculus 70 into the inner side of the basket wire 20. After then operator may pull the pushing portion 62, allowing the basket wire 20 to be led-in into the first tube 40.

The basket wire 20 may be led-in into the first tube 40 along the second tube 51 and the calculus 70 may be closely fixed to the tip end of the first tube 40 at the same time.

Then, the lithotripsy probe 55 coupled to an electrohydraulic lithotripsy shock wave generator may be pushed through a probe discharging portion 65, allowing the electrode 58 of the lithotripsy probe to be discharged from the second tube 51, so as to be close to or contacted to the calculus 70. In this state, a shock wave may be applied to the calculus.

At this time, the calculus 70 may be fixed by the basket wire 20, allowing applying the shock wave to the calculus accurately and strongly.

The calculus minutely destructed may be removed by natural evacuation. The calculus destructed into a size of 10 mm or under may be removed by the same method as when removing a calculus which has a long diameter of 10 mm or under.

The above operation may be performed once after a bile duct calculus of the first tube 40 is captured in the basket wire 20 inside the bile duct.

In the removal of a calculus like the above, when the calculus 70 may be captured by the basket wire 20 of the second tube 51 and pulled toward the first tube 40, the tube protecting portion 42 formed at the tip end of the first tube 40 may prevent the first tube 40 made of a plastic material from being damaged by a force added from the tip end of the first tube 40 when being pulled.

In addition, the tube protecting portion 42 may be made of a metal material, allowing to be shown on an X-ray image very well and consequently to make the operation performed easily.

According to the present invention, when applying the aforementioned configurations of the present invention, a user may be provided with a calculus removing device which has a lithotripsy probe capable of simultaneously destructing and removing the calculus formed in the human body regardless of the size of the calculus by optionally using attractivity or electricity through a lithotripsy probe.

Further, according to the present invention, the calculus removing device allows the insertion of a guide wire for guiding a basket catheter into the interior region of a second tube, wherein a plurality of the guide wires may be applied using structural features of the end of a first tube, so as to enhance fixability or send the guide wires to the directions that user desires.

Further, a calculus removing device according to the present invention may allow capturing and destructing various calculi using one device. The device thus may not require to use any of cholangioscopy, basket catheters and electrohydraulic lithotripters separately.

Further, a calculus removing device according to the present invention, may allow performing an operation directly while watching an X-ray image. The device thus may not require any of a high-priced endoscope for operating an electrohydraulic lithotripter separately and inserted into the endoscope, allowing identifying a calculus using the endoscope and subsequently destructing and removing the calculus.

Further, a calculus removing device according to the present invention may allow easy and simple lithotripsy by a lithotripsy probe differently from using the conventional mechanical lithotripsy basket catheter without frequent insertion.

Further, a calculus removing device according to the present invention may allow capturing and destructing various calculi using one device. The device thus may not require people necessary to operate conventionally devices needed for removing the respective calculi, allowing one person to perform an operation.

Further, since, in a state that a calculus is fixed by a capture means, the lithotripsy probe is placed at the center portion of the calculus and applies a shock to the calculus at the nearest distance, a shock wave may be transferred to the center portion of the calculus. Thus, it may excellent in the shock effect and involve no damage to the normal bile duct resulting from wobbling of the lithotripsy probe.

Further, the first tube is inserted into the bile duct, allowing the destruction of a calculus in the bile duct. Even if it is difficult to perform sphincterotomy, the calculus may be destructed at various times, allowing removing the calculus easily and simply by inserting the endoscope only once.

Further, calculi may be removed regardless of the order of the respective calculi which are developed on a near region and a far region.

Additionally, when a calculus and a cancer uncommonly present together, it may be possible to perform cytology test for a diagnosis of the cancer.

The detailed description of preferable embodiments of the present invention disclosed as the above is provided, allowing being embodied and implemented by those of ordinary skilled in the art.

Even though describing referring to preferable embodiments of the present invention in the above, those of ordinary skilled in the art may understand that the present invention may be modified and changed within the scope of the present invention.

For example, those of ordinary skilled in the art may use the respective elements described in the aforementioned embodiments by combination thereof.

Therefore, the present invention is not limited to the embodiments disclosed herein, but intends to grant the widest scope corresponding to principals and novel features disclosed herein.

The present invention may be embodied in any other specific forms within the scope of the concept and essential features. Therefore, the above detailed description should not be interpreted restrictively in all aspects but considered as examples.

The scope of the present invention should be determined by rational interpretation, and all modifications within the scope equivalent to the present invention should be included in the present invention.

The present invention is not limited to the embodiments disclosed herein, but intends to grant the largest scope corresponding to principals and novel features disclosed herein.

Further, embodiments may be configured by combination of claims which are not explicitly in citation relation with the scope of claimed inventions, or may be included as new claims by amendments after filing an application.

What is claimed is:

1. An calculus removing device comprising:
a first tube having an interior region;
a second tube which is inserted into the interior region of the first tube so as to move in the interior region;
a capture means of which one end is coupled to an end of the second tube, and which is led-in into the interior region of the first tube corresponding to the moving of the second tube, allowing capturing and fixing a calculus;
a lithotripsy probe which is inserted into an interior region of the second tube and contacts with the calculus fixed by the capture means, allowing applying an electric shock; and
a handle which is coupled to an end of the first tube, and moves the second tube and the lithotripsy probe independently, wherein
the capture means further comprises, at an opposite end, a head portion which is at least partially opened and has a diameter larger than that of the first tube,
a plurality of guide wires for guiding the calculus removing device is inserted through the interior region of the second tube,
the plurality of guide wires inserted is discharged to the outside through the head portion, and
the capture means is a basket configured with at least two or more wires having elasticity.

2. The calculus removing device of claim 1,
if a size of the calculus is less than a predetermined size, the calculus fixed by the capture means is removed as the handle is pulled, and
if a size of the calculus exceeds the predetermined size, the calculus fixed by the capture means is removed by the applied electrical shock.

3. The calculus removing device of claim 1,
the capture means is coupled with an end of the second tube using at least one of methods as follows;
a method which allows the insertion of the capture means formed at the end of the second tube, a method which allows the insertion of the capture means into a hole formed at the end of the second tube, and a method which allows the capture means in a state of being winded up around a member formed at the end of the second tube to be unwound corresponding to the rotation of the member and comes out to the outside.

4. The calculus removing device of claim 1:
the head portion further comprises, in an opened space, a separating member which is separated into a plurality of regions, wherein
the plurality of guide wires inserted is separated to the at least a portion of the plurality of regions allowing discharge to the outside, and
the separating member is detachable.

5. The calculus removing device of claim 4,
the separating member becomes thicker toward an end of the head portion, and the plurality of guide wires is bent at a predetermined angle using a thickness of the separating member allowing discharge to the outside.

6. A method for removing a calculus comprising steps of:
inserting a second tube into an interior region of a first tube so as to move;
leading-in a capture means coupled to an end of the second tube into the interior region of the first tube corresponding to the moving of the second tube;
capturing and fixing a calculus as the capture means is led-in into the interior region of the first tube; and
contacting a lithotripsy probe inserted into an interior region of the second tube with a calculus fixed by the capture means, allowing applying an electric shock; wherein
the capture means further comprises, at an opposite end, a head portion which is at least partially opened and has a diameter larger than that of the first tube,
a plurality of guide wires for guiding the calculus removing device is inserted through the interior region of the second tube,
the plurality of guide wires inserted is discharged to the outside through the head portion, and
the capture means is a basket configured with at least two or more wires having elasticity.

7. The method for removing a calculus of claim 6,
if a size of the calculus is less than a predetermined size, the calculus fixed by the capture means is removed as the handle is pulled, and
if a size of the calculus exceeds the predetermined size, the calculus fixed by the capture means is removed by the applied electrical shock.

8. The method for removing a calculus of claim 6,
the capture means is coupled with an end of the second tube using at least one of methods as follows;
a method which allows the insertion of the capture means formed at the end of the second tube, a method which allows the insertion of the capture means into a hole formed at the end of the second tube, and a method which allows the capture means in a state of being winded up around a member formed at the end of the second tube to be unwound corresponding to the rotation of the member and comes out to the outside.

9. The method for removing a calculus of claim 6,
the head portion further comprises, in an opened space, a separating member which is separated into a plurality of regions, wherein
the plurality of guide wires inserted is separated to the at least a portion of the plurality of regions, allowing discharge to the outside, and
the separating member is detachable.

10. The method for removing a calculus of claim 9,
the separating member becomes thicker toward an end of the head portion, and the plurality of guide wires is bent at a predetermined angle using a thickness of the separating member, allowing discharge to the outside.

* * * * *